(12) United States Patent
Son et al.

(10) Patent No.: US 12,257,461 B2
(45) Date of Patent: Mar. 25, 2025

(54) ULTRASOUND TREATMENT HEAD AND ULTRASOUND IMAGING AND TREATMENT METHOD USING SAME

(71) Applicant: IMGT CO., LTD., Seongnam-si (KR)

(72) Inventors: Keon Ho Son, Seongnam-si (KR); Young Bok Yu, Seoul (KR)

(73) Assignee: IMGT CO., LTD., Seongnam-si (KR)

( * ) Notice: Subject to any disclaimer, the term of this patent is extended or adjusted under 35 U.S.C. 154(b) by 172 days.

(21) Appl. No.: 17/923,510

(22) PCT Filed: May 6, 2021

(86) PCT No.: PCT/KR2021/005634
§ 371 (c)(1),
(2) Date: Nov. 4, 2022

(87) PCT Pub. No.: WO2021/225368
PCT Pub. Date: Nov. 11, 2021

(65) Prior Publication Data
US 2023/0191160 A1    Jun. 22, 2023

(30) Foreign Application Priority Data

May 8, 2020 (KR) .................. 10-2020-0055000
Nov. 2, 2020 (KR) .................. 10-2020-0144041

(51) Int. Cl.
*A61B 8/00* (2006.01)
*A61B 8/08* (2006.01)
(Continued)

(52) U.S. Cl.
CPC .................. *A61N 7/02* (2013.01); *A61B 8/08* (2013.01); *A61N 2007/0091* (2013.01)

(58) Field of Classification Search
None
See application file for complete search history.

(56) References Cited

U.S. PATENT DOCUMENTS 4,512,710 A * 4/1985 Flatau .................... B25J 9/1025
  414/735
9,573,000 B2   2/2017 Albright et al.
(Continued)

FOREIGN PATENT DOCUMENTS

KR   10-2010-0121277 A   11/2010
KR      10-1023657 B1    3/2011
(Continued)

OTHER PUBLICATIONS

Korean Office Action issued on Sep. 27, 2022 in corresponding Korean Patent Application No. 10-2020-0144041. (6 pages in Korean and 7 pages in English).

(Continued)

*Primary Examiner* — Patricia J Park
(74) *Attorney, Agent, or Firm* — NSIP Law

(57) ABSTRACT

An ultrasound treatment head and an ultrasound imaging and treatment method using the same are disclosed. The ultrasound treatment head according to an embodiment comprises: a structure including a treatment transducer and an imaging probe positioned at the center of the treatment transducer, the treatment transducer and the imaging probe being physically aligned; a first mechanism for steering the mechanical movement of the entire structure; and a second mechanism for steering the mechanical movement of either the imaging probe or the treatment transducer alone in the structure.

8 Claims, 17 Drawing Sheets

(51) Int. Cl.
*A61N 7/02* (2006.01)
*A61N 7/00* (2006.01)

(56) References Cited

U.S. PATENT DOCUMENTS

| | | | |
|---|---|---|---|
| 2008/0167555 A1* | 7/2008 | Qian | A61N 7/02 600/439 |
| 2012/0046592 A1 | 2/2012 | Albright et al. | |
| 2012/0238873 A1* | 9/2012 | Lacoste | A61B 8/4461 600/459 |
| 2019/0365348 A1* | 12/2019 | Toume | A61B 8/065 |
| 2020/0164231 A1* | 5/2020 | Cannata | A61B 34/30 |
| 2021/0153840 A1 | 5/2021 | Kellnberger et al. | |

FOREIGN PATENT DOCUMENTS

| | | |
|---|---|---|
| KR | 10-1263285 B1 | 5/2013 |
| KR | 10-2013-0106361 A | 9/2013 |
| KR | 10-2018-0003503 A | 1/2018 |
| WO | WO 2014/081108 A1 | 5/2014 |
| WO | WO 2016/126040 A1 | 8/2016 |
| WO | WO 2019/236606 A1 | 12/2019 |

OTHER PUBLICATIONS

Korean Decision to Grant a Patent issued on Mar. 8, 2023 in corresponding Korean Patent Application No. 10-2020-0144041. (2 pages in Korean and 2 pages in English).
International Search Report issued on Aug. 12, 2021 in counterpart of PCT/KR2021/005635 (4 pages in Korean).
Korean Office Action on Sep. 27, 2022 in corresponding Korean Patent Application No. 10-2020-0144041 (6 pages in Korean).

* cited by examiner

ULTRASOUND TREATMENT HEAD AND ULTRASOUND IMAGING AND TREATMENT METHOD USING SAME

CROSS-REFERENCE TO RELATED APPLICATIONS

This application is a U.S. national stage application of International Application No. PCT/KR2021/005634 filed on May 6, 2021, which claims the benefit under 35 USC 119 (a) of Korean Patent Application Nos. 10-2020-0055000 filed on May 8, 2020, and 10-2020-0144041 filed on Nov. 2, 2020, in the Korean Intellectual Property Office, the entire disclosure of which are incorporated herein by reference for all purposes.

TECHNICAL FIELD

The present invention is derived from research conducted as a part of the projected which supported by the Korea Medical Device Development Fund (KMDF) grant funded by the Korea government (the Ministry of Science and ICT, the Ministry of Trade, Industry and Energy, the Ministry of Health & Welfare, the Ministry of Food and Drug Safety) [Project No. 9991006682, KMDF_PR_20200901_0009, Research Project Title: Commercial development of market-leading pancreatic cancer fusion treatment ultrasound image-guided high-intensity focused ultrasound treatment device, Research Period: Mar. 1, 2022 to Dec. 31, 2022].

BACKGROUND ART

Ultrasound signals may be used to treat biological tissues such as cancer, tumors, lesions, or the like. Treatment using ultrasound is a method of treating a lesion by radiating ultrasound signals to the lesion of the human body. Ultrasound treatment can lessen a patient's trauma than general surgery or chemotherapy, and realize non-invasive treatment. For example, the ultrasound treatment is applied to liver cancer, bone sarcoma, breast cancer, pancreatic cancer, kidney cancer, soft tissue tumors, pelvic tumors, and the like.

DISCLOSURE

Technical Problem

The present invention is directed to providing an ultrasound treatment head that can accurately transmit ultrasound energy, expand a range of treatment, safely identify and treat a treatment area within a short period of time, and can be miniaturized, and an ultrasound imaging and treatment method using the same.

Technical Solution

One aspect of the present invention provides an ultrasound treatment head including a structure including a treatment transducer and an imaging probe positioned at a center of the treatment transducer, wherein the treatment transducer and the imaging probe are physically aligned, a first mechanism configured to steer mechanical movement of the entire structure, and a second mechanism configured to steer mechanical movement of either the imaging probe or the treatment transducer alone in the structure.

The first mechanism may include a structure rotation mechanism configured to steer rotation of the entire structure, and a structure tilting mechanism configured to steer tilting movement of the entire structure.

The structure rotation mechanism may include a first fixed pulley horizontally fixed to an upper end of the structure, a first motor formed to be spaced a preset interval from the first fixed pulley and configured to provide power for the rotation of the entire structure, a first motor pulley fixed to the first motor, and at least one first connection part configured to connect the first fixed pulley fixed to the structure to the first motor pulley fixed to the first motor to rotate the structure to which the first fixed pulley is fixed by rotation of the at least one first connection part when the first motor is driven, wherein, when the first motor is driven, the first motor pulley rotates the first fixed pulley through the at least one connection part that connects the first fixed pulley to the first motor pulley to rotate the imaging probe and the treatment transducer together.

The structure rotation mechanism may include a first gear horizontally fixed to an upper end of the structure, a first motor formed to be spaced a preset interval from the first gear and configured to provide power for the rotation of the entire structure, and a second gear coupled to the first motor to rotate, wherein, when the first motor is driven, the second gear directly rotates the first gear or rotates the first gear through at least one connection part that connects the first gear to the second gear to rotate the imaging probe and the treatment transducer together in the structure.

The structure tilting mechanism may include a second fixed pulley vertically fixed to one side surface of the structure, a second motor formed to be spaced a preset interval from the second fixed pulley and configured to provide power for tilting of the entire structure, a second motor pulley fixed to the second motor, and at least one second connection part configured to connect the second fixed pulley fixed to the structure to the second motor pulley fixed to the second motor to tilt the structure to which the second fixed pulley is fixed by rotation of the least one second connection part when the second motor is driven, wherein, when the second motor is driven, the second motor pulley tilts the second fixed pulley through at least one connection part that connects the second fixed pulley to the second motor pulley to tilt the imaging probe and the treatment transducer together.

The structure tilting mechanism may include a third gear vertically fixed to one side surface of the structure, a second motor formed to be spaced a preset interval from the third gear and configured to provide power for rotation of the entire structure, and a fourth gear coupled to the second motor to rotate, wherein, when the second motor is driven, the fourth gear directly rotates the third gear or rotates the third gear through at least one second connection part that connects the third gear to the fourth gear to tilt the imaging probe and the treatment transducer together in the structure.

The second mechanism may include an imaging probe rotation mechanism that steers rotation of the imaging probe alone.

The imaging probe rotation mechanism may include a third fixed pulley horizontally fixed to the imaging probe, a third motor formed to be spaced a preset interval from the third fixed pulley and configured to provide power for the rotation of the imaging probe alone, a third motor pulley fixed to the third motor, and a third connection part configured to connect the third fixed pulley fixed to the imaging probe to the third motor pulley fixed to the third motor to rotate the imaging probe to which the third fixed pulley is fixed by rotation of the third connection part when the third motor is driven, wherein, when the third motor is driven, the third motor pulley rotates the third fixed pulley through at least one connection part that connects the third fixed pulley to the third motor pulley to rotate the imaging probe alone.

The imaging probe rotation mechanism may include a fifth gear horizontally fixed to the imaging probe, a third motor formed to be spaced a preset interval from the fifth gear and configured to provide power for the rotation of the entire structure, and a sixth gear coupled to the third motor to rotate, wherein, when the third motor is driven, the sixth gear directly rotates the fifth gear or rotates the fifth gear through at least one third connection part that connects the fifth gear to the sixth gear to rotate the imaging probe alone.

The ultrasound treatment head may further include an electronic signal generator configured to drive the treatment transducer to radiate focused ultrasound waves, and a controller configured to drive the electronic signal generator and each of the first and second mechanisms to steer a focus of the focused ultrasound waves.

Another aspect of the present invention provides an ultrasound treatment head including a membrane having a structure that protects a focused ultrasound radiation surface of a treatment transducer, wherein an accommodation space for accommodating an ultrasound transmission medium is formed between the membrane and the focused ultrasound radiation surface, wherein the membrane has a preset thickness and is detached from or attached to a housing. The membrane may be mounted or detached in any one structure among a screw cap structure, a tightening structure, a clamp structure, a boa structure, and a buckle structure.

Advantageous Effects

According to the ultrasound treatment head and the ultrasound imaging and treatment method using the same according to an embodiment, ultrasound energy can be transmitted accurately, a range of treatment can be expanded, and a treatment area can be safely identified and treated within a short period of time.

For example, in treatment and the image acquisition using ultrasound, mechanical movement of a treatment transducer and an imaging probe can be steered without a separate user operation. In this case, the treatment transducer and the imaging probe can be mechanically steered together, and the treatment transducer and the imaging probe can be individually and mechanically steered. As mechanical steering, rotation movement and tilting movement for the treatment transducer and the imaging probe, and rotation movement for the imaging probe are possible.

Through mechanical adjustment including rotation and tilting to the structure that automatically aligns the physical positions of the treatment transducer and the imaging probe, a range of treatment can be expanded, and the treatment area can be identified and treated within a short period of time. Furthermore, since the ultrasound treatment head can be automatically aligned with a target, there is no need to change the treatment transducer for each treatment environment and various body environments every time.

Since a pully/belt structure, a gear structure, or a composite structure thereof are used in the mechanical steering control, it is possible to reduce noise, secure durability, and achieve miniaturization of an ultrasonic treatment head. By implementing the mechanical steering and the electronic steering together, accuracy can be increased.

Since a membrane for accommodating an ultrasonic transmission medium can be coupled or separated, it is convenient to use and it is possible to increase the sense of unity of the module.

MODES OF THE INVENTION

Figure 1:
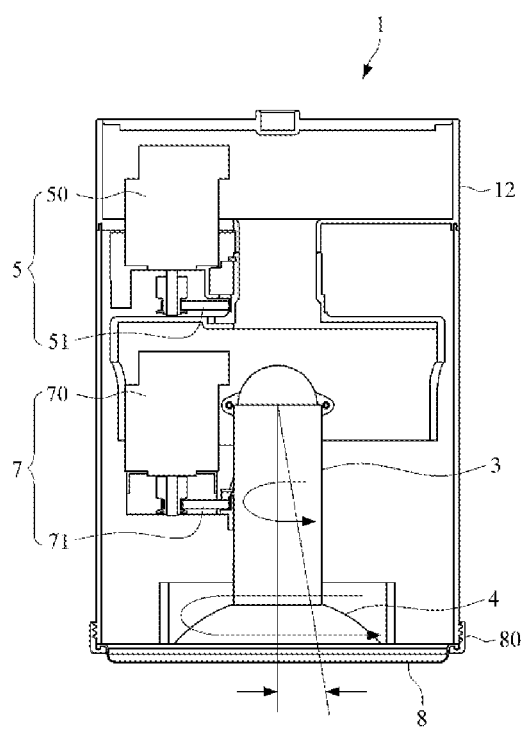
FIGS. 1 and 2 are cross-sectional views illustrating an ultrasound treatment head according to a first embodiment of the present invention.

Advantages and features of the present invention and methods of achieving the same will be clearly understood with reference to the accompanying drawings and embodiments described in detail below. However, the present invention is not limited to the embodiments to be disclosed below but may be implemented in various different forms. The embodiments are provided in order to fully explain the present embodiments and fully explain the scope of the present invention for those skilled in the art. The scope of the present invention is only defined by the appended claims. Like reference numerals refer to like elements throughout the specification.

In addition, when the embodiments of the present invention are described, if it is determined that detailed descriptions of known technology related to the present invention unnecessarily obscure the subject matter of the present invention, detailed descriptions thereof will be omitted. Some terms described below are defined by considering functions in the present invention, and meanings may vary depending on, for example, a user or operator's intentions or customs. Therefore, the meanings of terms should be interpreted based on the content throughout this specification.

In this case, it will be appreciated that each block of block diagrams and combinations of steps of flowcharts may be performed by computer program instructions (an execution engine). Since the computer program instructions may be loaded into a processor of a general-purpose computer, special purpose computer, or other programmable data processing devices, the instructions executed through the processor of the computer or other programmable data processing devices generate a means for performing the functions described in the block(s) of the block diagrams or the step(s) of the flowcharts.

Since the computer program instructions may be stored in a computer usable or computer readable memory that can be directed to a computer or other programmable data processing devices to implement functionality in a particular manner, the instructions stored in the computer usable or computer readable memory may produce a manufactured item containing an instruction means for performing the functions described in the block(s) of the block diagrams or the step(s) of the flowcharts.

Since the computer program instructions may also be installed in a computer or other programmable data processing devices, instructions for performing a series of operating steps on a computer or other programmable data processing devices to generate a computer-implemented process to be performed on the computer or other programmable data processing devices may provide steps for performing the functions described in the block(s) of the block diagrams or the step(s) of the flowcharts.

In addition, each block or step may represent a module, segment, or portion of code that includes one or more executable instructions for executing a specified logical function(s). It should also be noted that in some alternative implementations, the functions mentioned in the blocks or steps may occur out of order. For example, two blocks or steps illustrated in succession may in fact be executed substantially concurrently or the blocks may sometimes be executed in reverse order depending on the corresponding function.

Hereinafter, various embodiments of the present invention will be described in detail with reference to the accompanying drawings. However, the embodiments of the present invention may be modified into several different forms, and the scope of the present invention is not limited to the embodiments to be described below. The embodiments of the present invention are provided to fully explain the invention to those skilled in the art.

Figure 2:
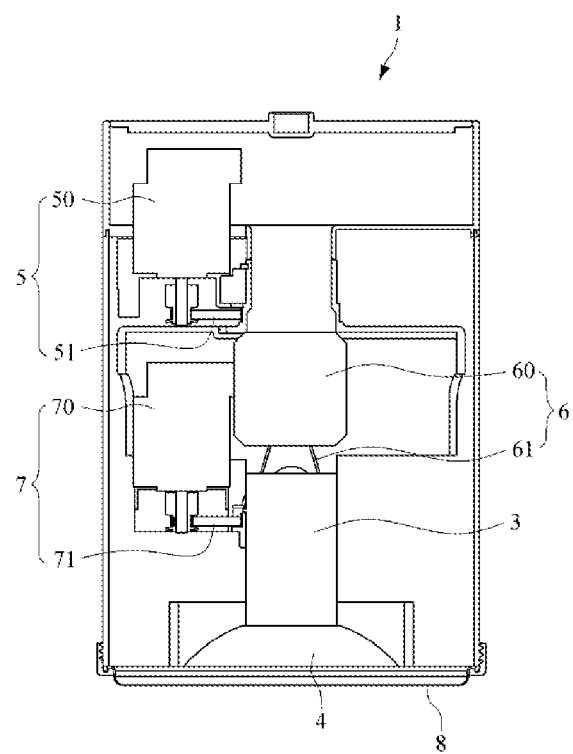

FIGS. 1 and 2 are cross-sectional views illustrating an ultrasound treatment head according to a first embodiment of the present invention.

Referring to FIGS. 1 and 2, an ultrasound treatment head 1 includes an imaging probe 3, a treatment transducer 4, a first mechanism, a second mechanism, a membrane 8, and a housing 12. Positions of the imaging probe 3 and the treatment transducer 4 are physically aligned and then the imaging probe 3 and the treatment transducer 4 are assembled to provide a structure 2. The first mechanism may include a structure rotation mechanism 5 and a structure tilting mechanism 6, and the second mechanism may include an imaging probe rotation mechanism 7.

The treatment transducer 4 is configured to radiate focused ultrasound waves for patient treatment. As illustrated in FIG. 1, the treatment transducer 4 may have a focused ultrasound radiation surface that is formed in a concave curved surface shape with the center of a lower portion of the treatment transducer 4 as an apex. In this case, the focused ultrasound radiation surface may have a predetermined thickness and may be formed to have a substantially hemispherical shape. The treatment transducer 4 generates a focused ultrasound (FUS) signal to focus on a treatment area. The treatment transducer 4 may have a structure of an array composed of a plurality of treatment transducers, and the plurality of treatment transducers constituting the array may be arranged randomly.

The treatment transducer 4 may be used for treatment purposes such as tissue destruction, drug delivery, and the like, which are treatments using ultrasound imaging called ultrasound image-guided therapy. As one of the ultrasound image-guided therapies, there is a treatment that more accurately hits a specific treatment area (e.g., cancer cells) with a therapeutic agent. For example, when nanoparticles containing a therapeutic agent are delivered to a treatment area through a blood vessel by intravenous injection or the like and then the therapeutic agent-containing nanoparticles are exposed to ultrasonic energy that is harmless to the human body through the treatment transducer 4, the nanoparticles burst and the therapeutic agent contained in the nanoparticles is delivered to a specific treatment area. Such a method is a treatment method in which a concentration of a therapeutic agent is intensively increased in a specific treatment area, which can increase the efficacy of existing therapeutic agents several times. However, the present invention is not limited to drug delivery, and can be applied to any ultrasound technology capable of ultrasound treatment. The present invention may also be applied to various treatment methods such as thermal treatment, nerve stimulation, and the like in the field of drug delivery.

The imaging probe 3 is for acquiring a diagnostic image of a subject. An operator may perform a focused ultrasound treatment while checking the diagnostic image acquired by the imaging probe 3. The imaging probe 3 may be configured to transmit an ultrasound signal to the subject and receive the ultrasound signal reflected by the subject. For example, the imaging probe 3 may be configured by embedding a piezoelectric element or the like in a cylindrical casing. Ultrasound waves may be transmitted or received through a lower surface of the imaging probe 3. The imaging probe 3 may be inserted to pass through a center of the focused ultrasound radiation surface of the treatment transducer 4. To this end, an insertion hole for insertion of the imaging probe 3 may be formed in the center of the focused ultrasound radiation surface of the treatment transducer 4.

The housing 12 accommodates the components of the ultrasound treatment head 1. In an embodiment, the housing 12 may have an open lower side, and the focused ultrasound radiation surface of the treatment transducer 4 may be exposed through the open lower side. The focused ultrasound radiation surface may be formed such that edges of the focused ultrasound radiation surface are coupled to a lower opening of the housing 12 to block the lower opening of the housing 12.

The membrane 8 is mounted on the housing 12 to protect the ultrasound radiation surface. An accommodation space for accommodating an ultrasound transmission medium is formed between the membrane 8 and the focused ultrasound radiation surface. The ultrasound transmission medium may be made of degassed water or the like. For example, the membrane 8 may be formed to enclose the lower opening and a portion of a side surface of the housing 12, and may be coupled to the side surface of the housing 12 in a sealed state. Since the membrane 8 may be coupled to the edges of the ultrasound radiation surface of the treatment transducer 4 in a sealed state, the present invention is not limited to the exemplary embodiment.

The membrane 8 according to an embodiment has a preset thickness and is detached from or attached to the housing 12. For detachment or attachment, the membrane 8 may be mounted or detached in any one structure among a screw cap structure, a tightening structure, a clamp structure, a boa structure, and a buckle structure. The screw cap structure is similar to a bottle cap structure. Due to the structure in which the membrane 8 is easily detached or attached, the membrane 8 may be easily replaced, and may have a simple waterproof sealing structure.

The membrane 8 may be made of a material having an acoustic impedance similar to that of the ultrasound transmission medium, a small ultrasound transmission loss, and excellent elasticity. For example, the membrane 8 may be made of a material such as ethylene propylene (EPDM) rubber, latex rubber, silicone rubber, or the like. The membrane 8 has a shape as illustrated in FIG. 1 in a state in which the ultrasonic transmission medium is not accommodated in the accommodation space. In such a state, when the accommodation space is filled with a set amount of the ultrasound transmission medium, the membrane 8 may be changed to a substantially hemispherical shape.

In a state in which the ultrasound treatment head 1 is placed above a patient and the membrane 8 is brought into contact with the patient's skin, the ultrasound treatment head 1 may radiate focused ultrasound waves through the treatment transducer 4. Then, the focused ultrasound waves may be radiated to the patient's lesion portion through the ultrasound transmission medium between the focused ultrasound radiation surface and the membrane 8.

The ultrasound treatment head 1 according to an embodiment may steer mechanical movement of the entire structure through the first mechanism with respect to the structure in which the imaging probe 3 and the treatment transducer 4 are physically aligned, and steer mechanical movement of either the imaging probe or the treatment transducer alone in the structure through the second mechanism.

The first mechanism may include the structure rotation mechanism 5 that steers rotation of the entire structure, and the structure tilting mechanism 6 that steers tilting movement of the entire structure. The second mechanism may include the imaging probe rotation mechanism 7 that steers rotation of the imaging probe 3 alone.

The structure rotation mechanism 5, the structure tilting mechanism 6, and the imaging probe rotation mechanism 7 may perform mechanical steering using a pulley/belt structure, a gear structure, a composite structure, and the like. The composite structure is a mixture of a pully/belt structure and a gear structure, and for example, the structure rotation mechanism 5 has a pully and connection part structure, and the structure tilting mechanism 6 has a gear structure.

Hereinafter, a mechanical steering operation of the ultrasound treatment head using a pully/belt structure according to the first embodiment of the present invention will be described with reference to FIG. 2.

Referring to FIG. 2, the ultrasound treatment head 1 may provide a mechanical movement function for the entire structure including the imaging probe 3 and the treatment transducer 4, and provide a mechanical movement function for either the imaging probe 3 or the treatment transducer 4 alone. For example, the ultrasound treatment head 1 may provide a mechanical rotation (Pan) function and a mechanical tilting (Tilt) function for the entire structure including the imaging probe 3 and the treatment transducer 4, and provide a mechanical rotation (Pan) function for the imaging probe 3 or the treatment transducer 4 alone. The connection part may be used for the mechanical movement described above.

For example, the ultrasound treatment head 1 has a structure of a first motor 50 and a first connection part 51 in order to provide the mechanical rotation (Pan) function for the entire structure, has a structure of a second motor 60 and a second connection part 61 in order to provide the mechanical tilting (Tilt) function for the entire structure, and has a structure of a third motor 70 and a third connection part 71 in order to provide the rotation (Pan) function for the imaging probe 3 alone. In this case, each of the connection parts 51, 61, and 71 may be a belt.

Figure 3:
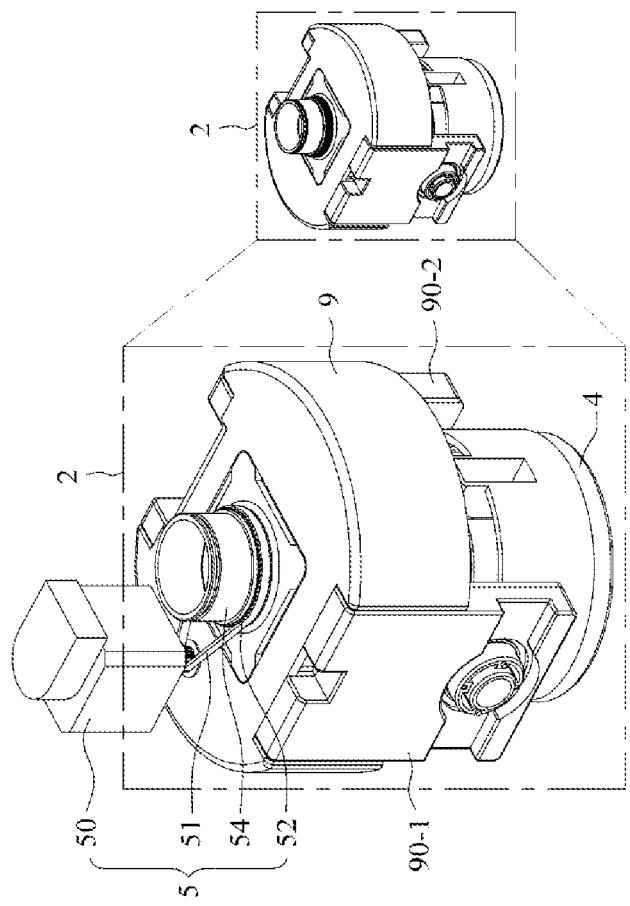
FIG. 3 is a view illustrating a configuration of a structure according to the first embodiment of the present invention.
Figure 4:
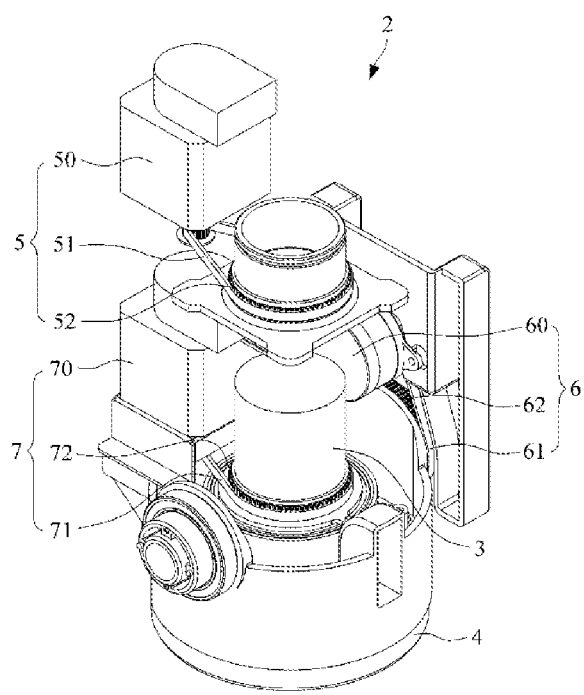
FIG. 4 is a view illustrating a configuration of the structure from which a case is removed according to the first embodiment of the present invention.

FIG. 3 is a view illustrating a configuration of a structure according to the first embodiment of the present invention, and FIG. 4 is a view illustrating a configuration of the structure from which a case is removed according to the first embodiment of the present invention.

Referring to FIGS. 3 and 4, the imaging probe 3 and the treatment transducer 4 are aligned and constrained within the structure 2. To this end, the structure 2 includes an aligner for physically aligning the imaging probe 3 and the treatment transducer 4 within the structure 2. The aligner may include, for example, a case 9 for accommodating at least a portion of the structure 2, and fixing devices 90-1 and 90-2 which are erected vertically to fix the case 9 and the structure 2. In this case, a first fixing device 90-1 fixes the case 9 and the structure 2 by being coupled to the case 9 and the structure 2. A second fixing device 90-2 fixes the case 9 by being coupled only to the case 9, and has a structure in which the second motor 60 mounted on the second fixing device 90-2 is connected to the structure 2 through the second connection part 61, and thus the structure 2 is tiltable left and right by the rotation of the second connection part 61 when the second motor 60 is driven. The second connection part 61 may be a belt.

On an upper end of the case 9, a fixed shaft 54 and a first fixed pulley 52 fixed to the fixed shaft 54 are formed, and the first fixed pulley 52 has a structure of being wound together with a motor pulley of the first motor 50 by the first connection part 51. When the first motor 50 rotates, the first fixed pulley 52 connected to the first connection part 51 is rotated by the rotation of the first connection part 51, and thus, at the same time, the structure 2 including the treatment transducer 4 and the imaging probe 3 is rotated. The first connection part 51 may be a belt. An embodiment of the rotation of the structure will be described below with reference to FIGS. 5 and 6.

In the structure 2, the second motor 60 is mounted on the second fixing device 90-2 formed in a vertical direction. When the second motor 60 is driven, the structure 2 fixed to a second fixed pulley 62 is tilted left and right by the rotation of the second connection part 61. The second connection part 61 may be a belt. An embodiment of the tilting of the structure will be described below with reference to FIGS. 7 to 9.

Meanwhile, a third fixed pulley 72 is fixed to one end (e.g., lower end) of the imaging probe 3, and the third fixed pulley 72 has a structure of being wound together with a motor pulley of the third motor 70 by the third connection part 71. When the third motor 70 rotates, the third fixed pulley 72 connected to the third connection part 71 may be rotated by the rotation of the third connection part 71, and thus the imaging probe 3 alone may be rotated. The third connection part 71 may be a belt. An embodiment of the rotation of the imaging probe 3 alone will be described below with reference to FIG. 10.

Figure 5:
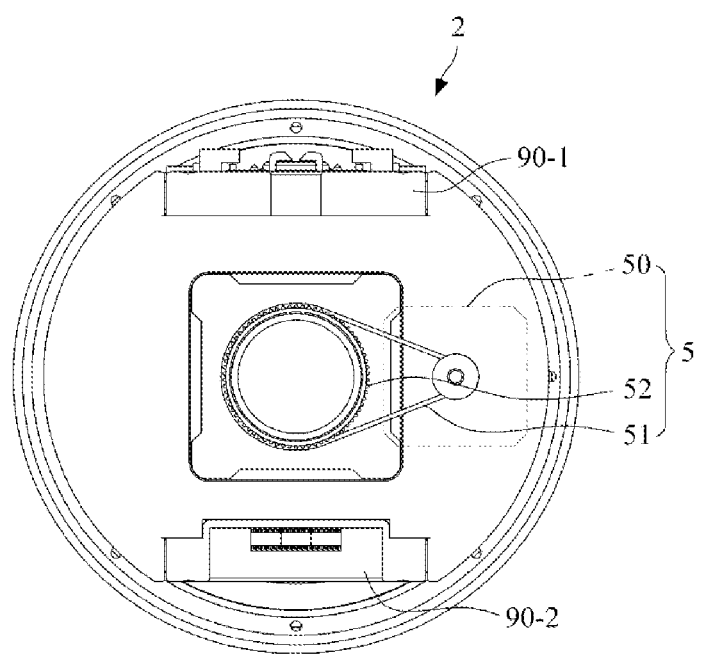
FIGS. 5 and 6 are views illustrating an upper surface of the structure to show an overall rotation operation of the structure according to the first embodiment of the present invention.
Figure 6:
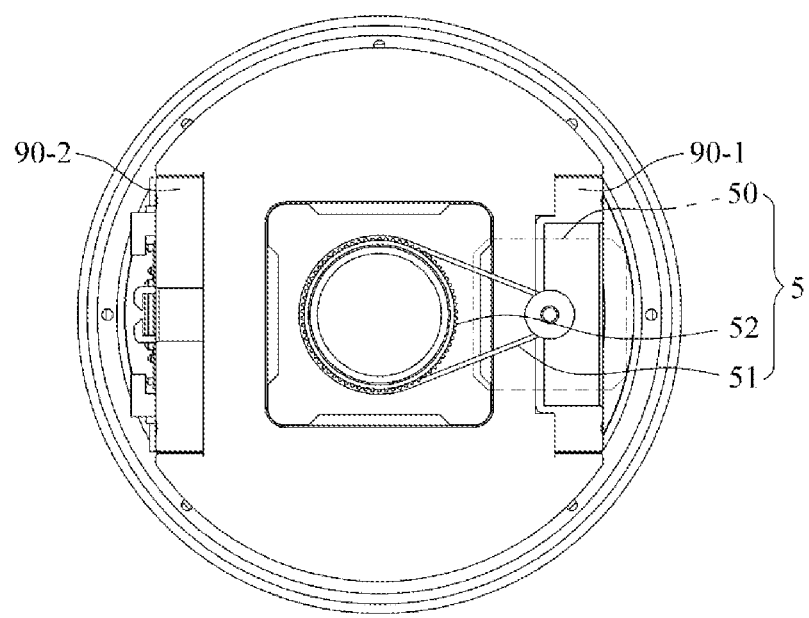

FIGS. 5 and 6 are views illustrating an upper surface of the structure to show an overall rotation operation of the structure according to the first embodiment of the present invention.

Referring to FIGS. 5 and 6, the entire structure 2 may rotate 180 degrees in a clockwise (CW) direction and 180 degrees in a counterclockwise (CCW) direction, and thus freely rotate a total of 360 degrees. For example, when the first motor 50 rotates 90 degrees in the CW direction in the structure 2 of FIG. 5, the first fixed pulley 52 connected to the first connection part 51 rotates 90 degrees in the CW direction by the rotation of the first connection part 51, as illustrated in FIG. 6, and thus the structure 2 on which the first fixed pulley 52 is mounted rotates 90 degrees in the CW direction.

Figure 7:
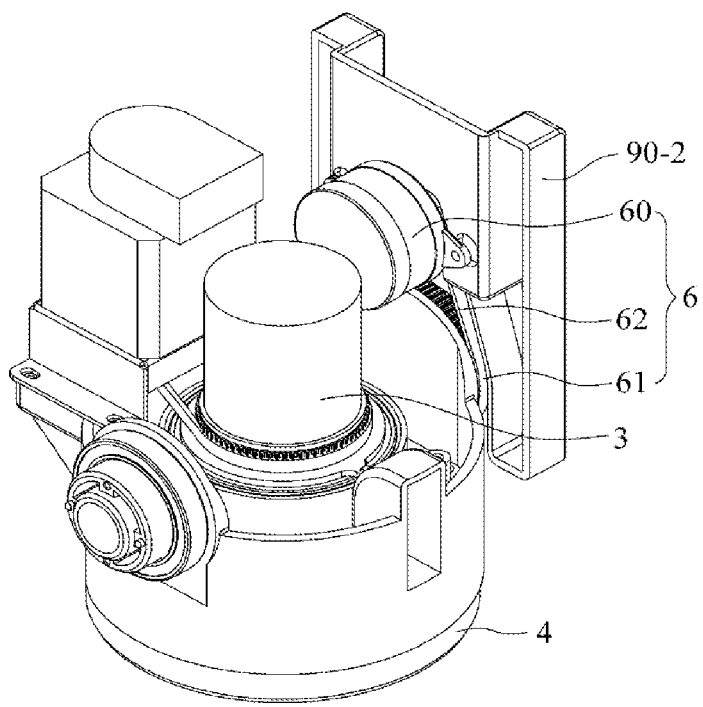
FIGS. 7 to 9 are views illustrating a configuration of the structure to show an overall tilting operation of the structure according to the first embodiment of the present invention.
Figure 8:
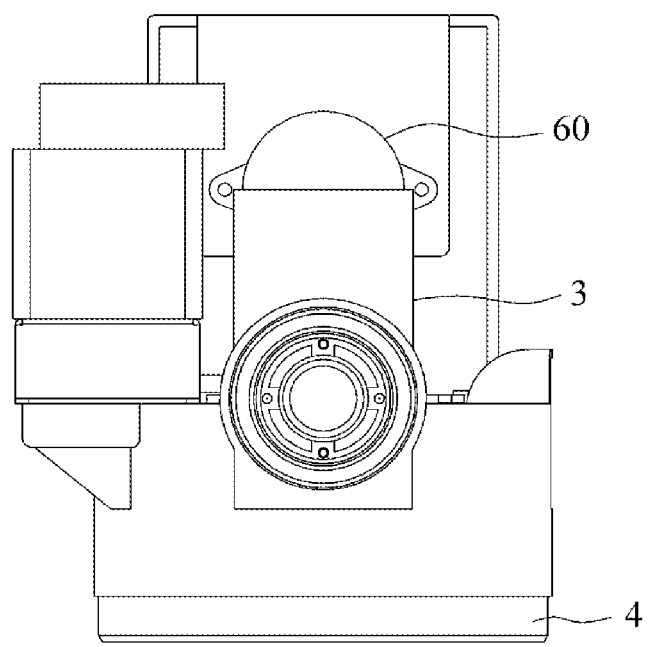
Figure 9:
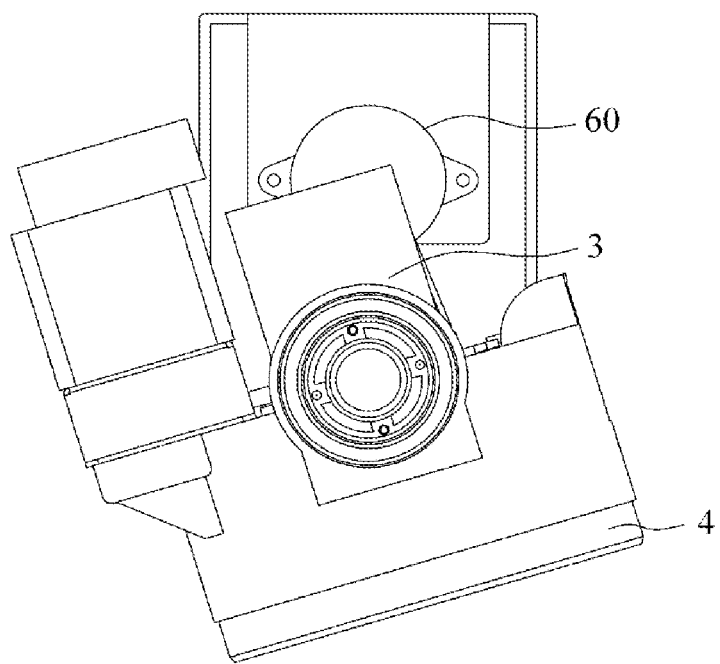

FIGS. 7 to 9 are views illustrating a configuration of the structure to show an overall tilting operation of the structure according to the first embodiment of the present invention.

Referring to FIGS. 7 to 9, the second motor 60 is mounted on the second fixing device 90-2 formed in the vertical direction. In this case, when the second motor 60 is driven, the structure 2 fixed to the second fixed pulley 62 is tilted left and right by the rotation of the second connection part 61. In this case, a tilting angle may be 10 degrees left and right, but the present invention is not limited thereto.

Figure 10:
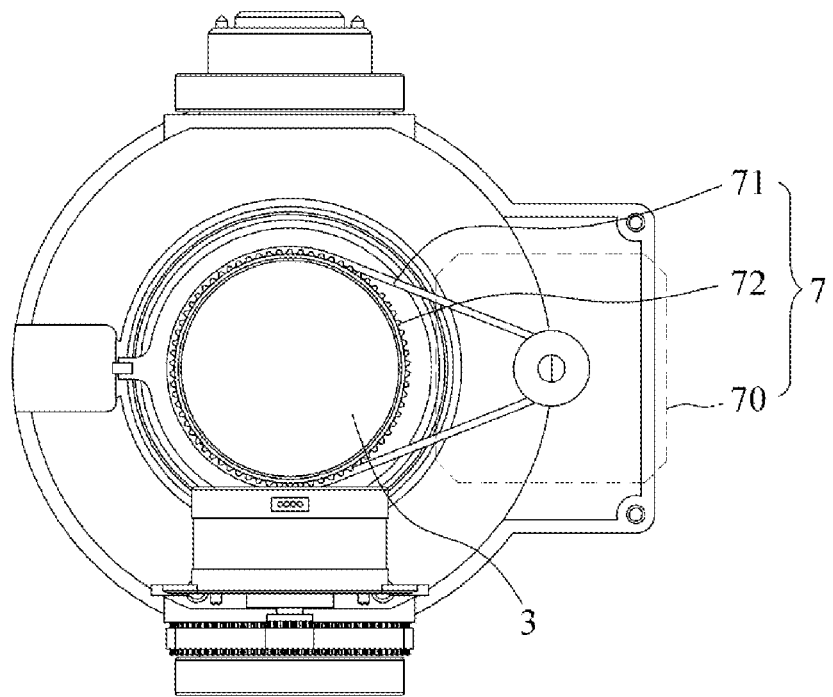
FIG. 10 is a view illustrating an internal structure of the ultrasound treatment head to show a rotation operation of an imaging probe according to the first embodiment of the present invention.

FIG. 10 is a view illustrating an internal structure of the ultrasound treatment head to show a rotation operation of an imaging probe according to the first embodiment of the present invention.

Referring to FIG. 10, the third fixed pulley 72 is fixed to one end (e.g., lower end) of the imaging probe 3, and the third fixed pulley 72 has a structure of being wound together with the motor pulley of the third motor 70 by the third connection part 71. When the third motor 70 rotates, the third fixed pulley 72 connected to the third connection part 71 may be rotated by the rotation of the third connection part 71, and thus the imaging probe 3 alone may be rotated.

Figure 11:
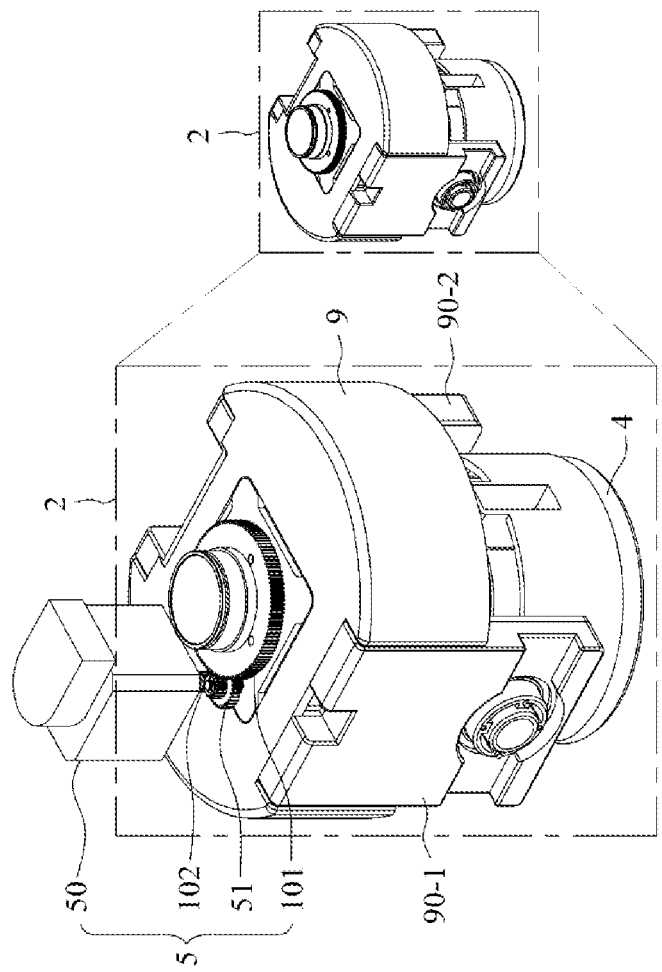
FIG. 11 is a view illustrating a configuration of a structure according to a second embodiment of the present invention.
Figure 12:
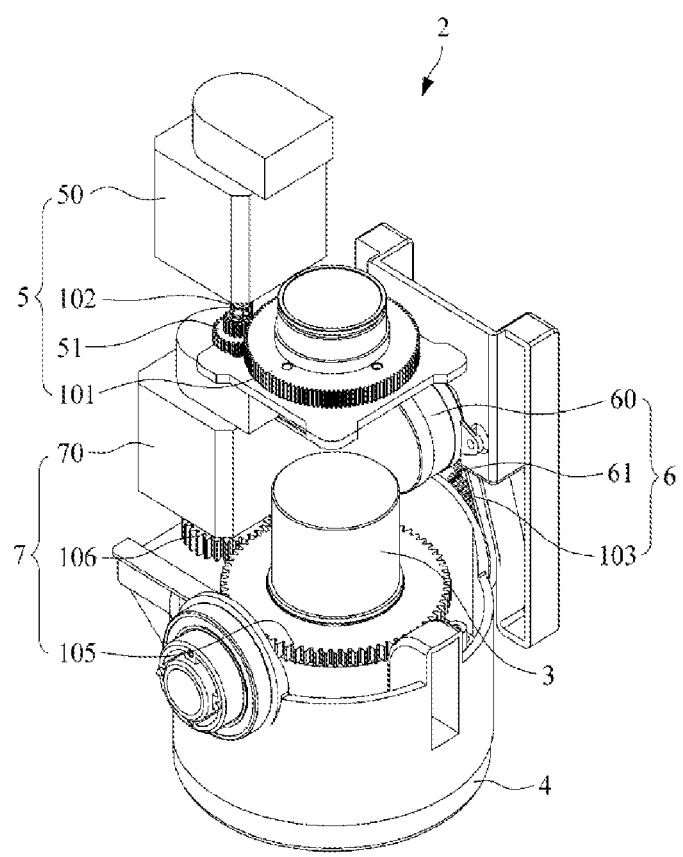
FIG. 12 is a view illustrating a configuration of the structure from which a case is removed according to the second embodiment of the present invention.

FIG. 11 is a view illustrating a configuration of a structure according to a second embodiment of the present invention, and FIG. 12 is a view illustrating a configuration of the structure from which a case is removed according to the second embodiment of the present invention.

Content different from that of the first embodiment of FIGS. 3 and 4 will be mainly described with reference to FIGS. 11 and 12.

Referring to FIGS. 11 and 12, a structure rotation mechanism 5 includes a first gear 101, a first motor 50, and a second gear 102, and may include at least one first connection part 51. The first connection part 51 may be a gear.

The first gear 101 is fixedly formed on an upper end of a structure 2 in a horizontal direction. The first motor 50 is spaced a preset interval from the first gear 101 to provide power for rotation of the entire structure. The second gear 102 is coupled to the first motor 50 to rotate. In this case, when the first motor 50 is driven, the second gear 102 directly rotates the first gear 101 or rotates the first gear 101 through the at least one first connection part 51 that connects the first gear 101 to the second gear 102 to rotate the imaging probe 3 and the treatment transducer 4 together in the structure 2.

A structure tilting mechanism 6 includes a third gear 103, a second motor 60, and a fourth gear (not illustrated), and may include at least one second connection part 61. The second connection part 61 may be a gear.

The third gear 103 is fixedly formed on one side surface of the structure 2 in a vertical direction. The second motor 60 is spaced a preset interval from the third gear 103 to provide power for rotation of the entire structure. The fourth gear (not illustrated) is coupled to the second motor 60 to rotate. In this case, when the second motor 60 is driven, the fourth gear (not illustrated) directly rotates the third gear 103 or rotates the third gear 103 through the at least one second connection part 61 that connects the third gear 103 to the fourth gear (not illustrated) to tilt the imaging probe 3 and the treatment transducer 4 together in the structure 2.

An imaging probe rotation mechanism 7 includes a fifth gear 105, a third motor 70, and a sixth gear 106, and may include at least one third connection part (not illustrated). The third connection part (not illustrated) may be a gear.

The fifth gear 105 is fixedly formed on the imaging probe 3 in the horizontal direction. The third motor 70 is spaced a preset interval from the fifth gear 105 to provide power for rotation of the entire structure. The sixth gear 106 is coupled to the third motor 70 to rotate. In this case, when the third motor 70 is driven, the sixth gear 106 directly rotates the fifth gear 105 or rotates the fifth gear 105 through the at least one third connection part (not illustrated) that connects the fifth gear 105 to the sixth gear 106 to rotate the imaging probe 3 alone.

Figure 13:
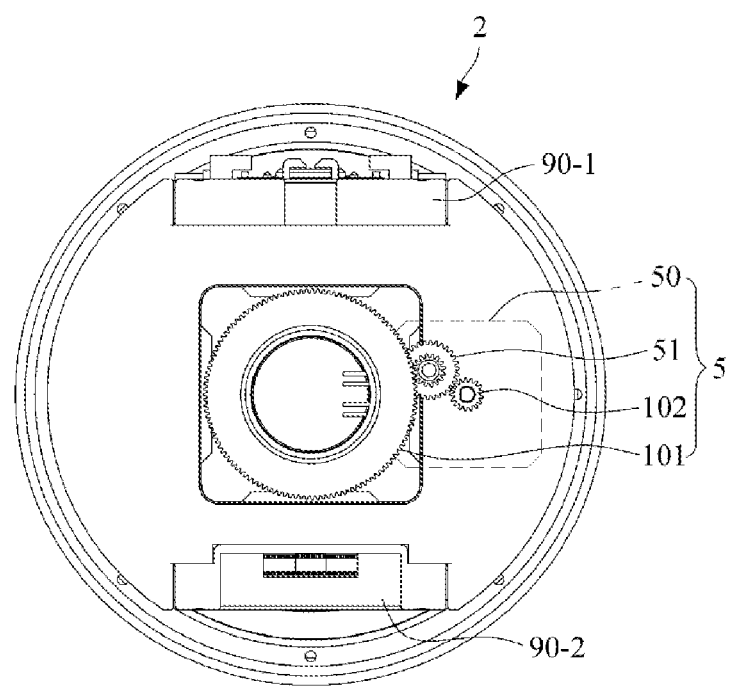
FIGS. 13 and 14 are views illustrating an upper surface of the structure to show an overall rotation operation of the structure according to the second embodiment of the present invention.
Figure 14:
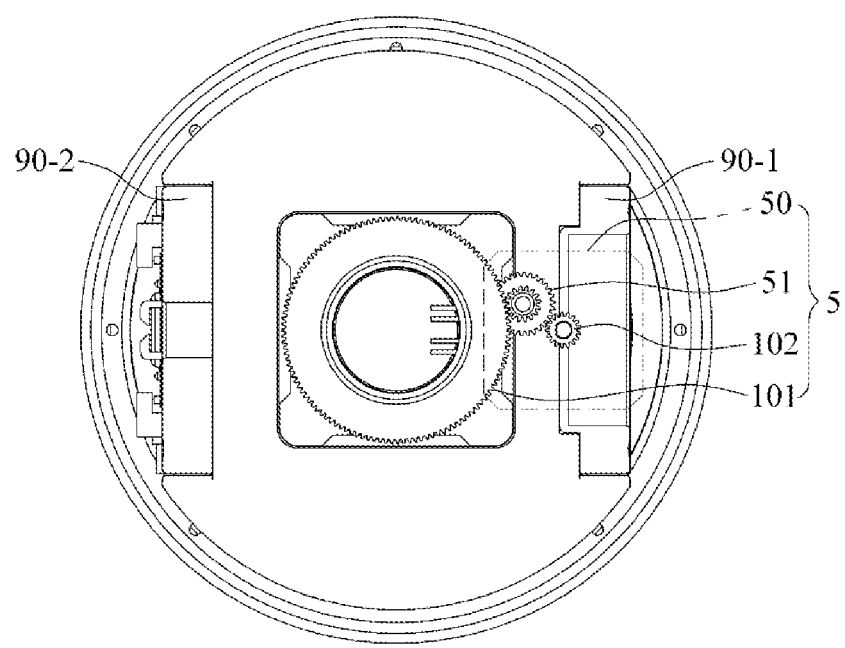

FIGS. 13 and 14 are views illustrating an upper surface of the structure to show an overall rotation operation of the structure according to the second embodiment of the present invention.

Content different from that of the first embodiment of FIGS. 5 and 6 will be mainly described with reference to FIGS. 13 and 14.

Referring to FIGS. 13 and 14, the entire structure 2 may rotate 180 degrees in a CW direction and 180 degrees in a CCW direction, and thus freely rotate a total of 360 degrees. For example, when the first motor 50 rotates 90 degrees in the CW direction in the structure 2 of FIG. 13, the second gear 102 rotates the first gear 101 90 degrees in the CW direction through the at least one first connection part 51 that connects the first gear 101 to the second gear 102 when the first motor 50 is driven, as illustrated in FIG. 14, and thus the structure 2 rotates 90 degrees in the CW direction.

Figure 15:
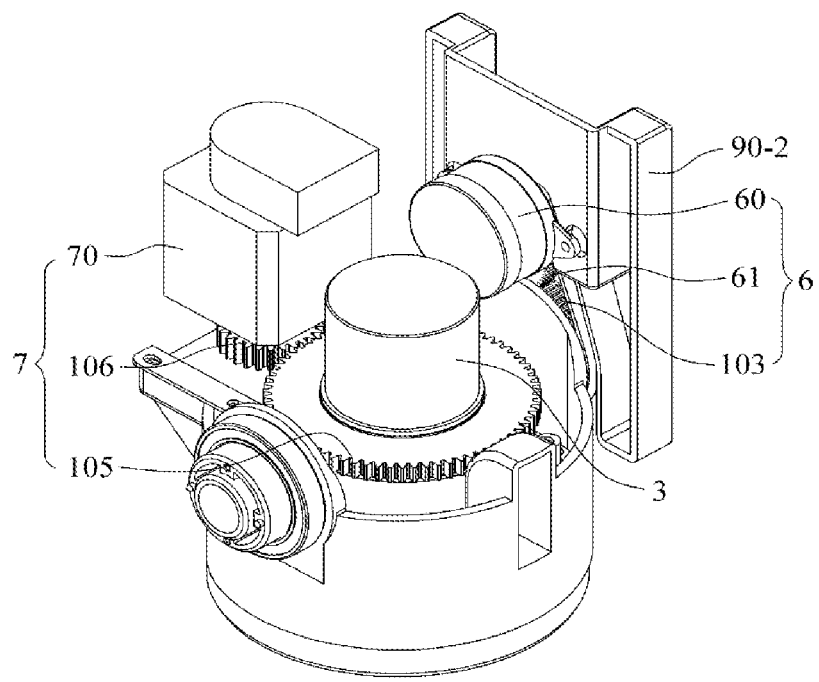
FIG. 15 is a view illustrating a configuration of the structure to show an overall tilting operation of the structure, and an internal structure of the ultrasound treatment head to show a rotation operation of an imaging probe according to the second embodiment of the present invention.

FIG. 15 is a view illustrating a configuration of the structure to show an overall tilting operation of the structure, and an internal structure of the ultrasound treatment head to show a rotation operation of an imaging probe according to the second embodiment of the present invention.

Content different from that of the first embodiment of FIGS. 7 to 10 will be mainly described with reference to FIGS. 15 and 16.

Figure 16:
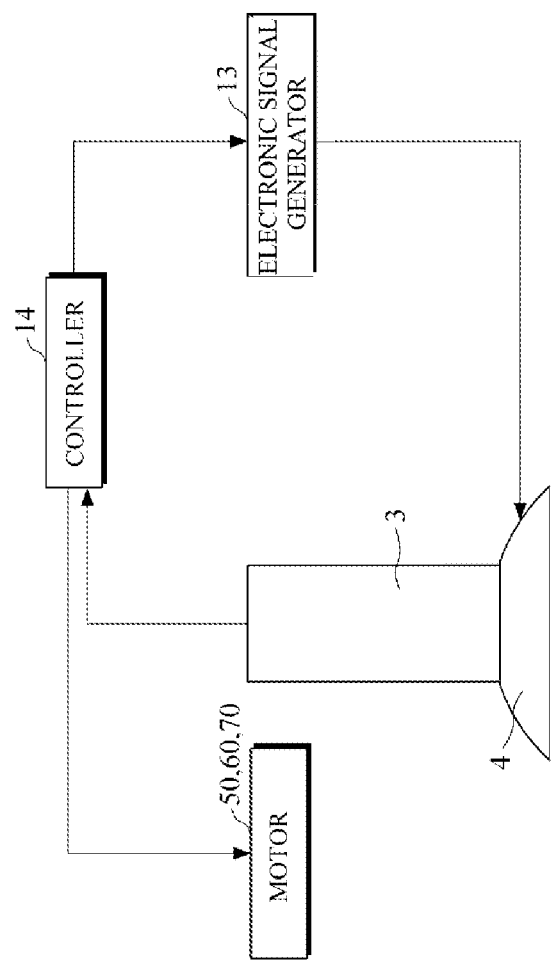
FIG. 16 is a view illustrating a configuration of an ultrasound treatment head in an operating state according to an embodiment of the present invention.

Referring to FIGS. 15 and 16, the second motor 60 is mounted on a second fixing device 90-2 formed in the vertical direction. In this case, when the second motor 60 is driven, the fourth gear (not illustrated) directly rotates the third gear 103 or rotates the third gear 103 through the at least one second connection part 61 that connects the third gear 103 to the fourth gear (not illustrated) to tilt the structure 2 left and right. In this case, a tilting angle may be 10 degrees left and right, but the present invention is not limited thereto.

When the third motor 70 is driven, the sixth gear 106 directly rotates the fifth gear 105 or rotates the fifth gear 105 through at least one third connection part (not illustrated) that connects the fifth gear 105 to the sixth gear 106 to rotate the imaging probe 3 alone.

FIG. 16 is a view illustrating a configuration of an ultrasound treatment head in an operating state according to an embodiment of the present invention.

Referring to FIG. 16, the ultrasound treatment head further includes an electronic signal generator 13 and a controller 14 in addition to the components of FIGS. 1 and 2.

The electronic signal generator 13 is configured to drive the treatment transducer 4 to radiate focused ultrasound waves. The controller 14 is configured to drive the electronic signal generator 13 and each of the motors 50, 60, and 70 of the mechanisms to steer a focus of the focused ultrasound waves. The controller 14 may be, for example, a programmed computer or a microcontroller. The controller 14 may receive image data from the imaging probe 3 to automatically perform steering. For example, the controller 14 may drive the electronic signal generator 13 and each of the motors 50, 60, and 70 of the mechanisms to compensate for physiological movements of a target while the focus follows a predetermined path and scans a target area. The steering through the electronic signal generator 13 performed by the controller 14 corresponds to electronic steering, and the steering through the mechanisms performed by the controller 14 corresponds to mechanical steering. That is, the ultrasound treatment head according to an embodiment may use a hybrid combination of electronic steering and mechanical steering.

Figure 17:
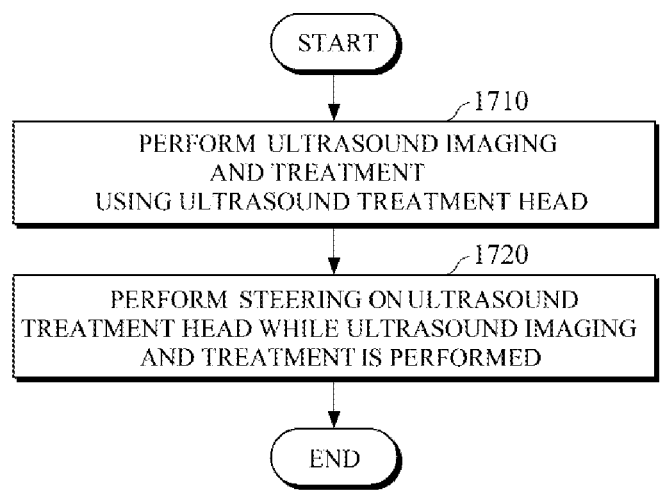
FIG. 17 is a flowchart illustrating an ultrasound imaging and treatment method according to an embodiment of the present invention.

FIG. 17 is a flowchart illustrating an ultrasound imaging and treatment method according to an embodiment of the present invention.

Referring to FIGS. 1 and 17, the ultrasound imaging and treatment method includes performing ultrasound imaging and treatment using an ultrasound treatment head (1710), and performing steering on the ultrasound treatment head while the ultrasound imaging and treatment is performed (1720). In the performing of the steering on the ultrasound treatment head (1720), the structure in which the treatment transducer 4 and the imaging probe 3 are aligned in the ultrasound treatment head 1 may be mechanically steered. For example, the ultrasound treatment head 1 may use the pully and first connection part 51 structure or use the gear structure to steer the mechanical rotation of the entire structure, and may use the pully and second connection part 61 structure or use the gear structure to steer the mechanical tilting movement of the entire structure. Furthermore, the ultrasound treatment head 1 may steer the physical rotation of either the imaging probe 3 or the treatment transducer 4 alone in the structure. For example, the ultrasound treatment head 1 may use the pully and third connection part 71 structure or use the gear structure to mechanically steer the imaging probe 3 alone so that an image of a treatment area can be acquired using the ultrasound waves radiated from the imaging probe 3.

While the present invention has been particularly described with reference to the exemplary embodiments, it will be understood by those skilled in the art that various changes in form and details may be made without departing from the spirit and scope of the present invention. Therefore, the exemplary embodiments should be considered in a descriptive sense only and not for purposes of limitation. The scope of the invention is defined not by the detailed description of the invention but by the appended claims and encompasses all modifications and equivalents that fall within the scope of the appended claims and will be construed as being included in the present invention.

The invewntion claimed is:

1. An ultrasound treatment head comprising:
a housing configured to accommodate components of the ultrasound treatment head;
a structure including a treatment transducer and an imaging probe positioned at a center of the treatment transducer, wherein the treatment transducer and the imaging probe are physically aligned;
an aligner configured to physically align the imaging probe and the treatment transducer within the structure, including a case for accommodating at least a portion of the structure;
a first mechanism configured to steer mechanical movement of an entire structure including the treatment transducer and the imaging probe in the housing; and
a second mechanism configured to steer mechanical movement of either the imaging probe or the treatment transducer alone in the structure,
wherein the first mechanism includes:
a structure rotation mechanism configured to steer rotation of the entire structure including the treatment transducer and the imaging probe, by a pulley or a gear horizontally fixed to an upper end of the structure to rotate the imaging probe and the treatment transducer together; and
a structure tilting mechanism configured to steer tilting movement of the entire structure including the treatment transducer and the imaging probe, by a pulley or a gear vertically fixed to one side surface of the structure to tilt the imaging probe and the treatment transducer together,
wherein the second mechanism includes:
an imaging probe rotation mechanism that steers rotation of the imaging probe alone, by a pulley or a gear horizontally fixed to the imaging probe in the structure.

2. The ultrasound treatment head of claim 1, wherein the structure rotation mechanism includes:
a first fixed pulley horizontally fixed to the upper end of the structure;
a first motor formed to be spaced a preset interval from the first fixed pulley and configured to provide power for the rotation of the entire structure;
a first motor pulley fixed to the first motor; and
at least one first connection part configured to connect the first fixed pulley fixed to the structure to the first motor pulley fixed to the first motor to rotate the structure to which the first fixed pulley is fixed by rotation of the at least one first connection part when the first motor is driven;
wherein, when the first motor is driven, the first motor pulley rotates the first fixed pulley through the at least one connection part that connects the first fixed pulley to the first motor pulley to rotate the imaging probe and the treatment transducer together.

3. The ultrasound treatment head of claim 1, wherein the structure rotation mechanism includes:
a first gear horizontally fixed to the upper end of the structure;
a motor formed to be spaced a preset interval from the first gear and configured to provide power for the rotation of the entire structure; and
a second gear coupled to the motor to rotate,
wherein, when the motor is driven, the second gear directly rotates the first gear or rotates the first gear through at least one connection part that connects the first gear to the second gear to rotate the imaging probe and the treatment transducer together in the structure.

4. The ultrasound treatment head of claim 1, wherein the structure tilting mechanism includes:
a fixed pulley vertically fixed to one side surface of the structure;

a motor formed to be spaced a preset interval from the fixed pulley and configured to provide power for tilting of the entire structure;
a motor pulley fixed to the motor; and
at least one connection part configured to connect the fixed pulley fixed to the structure to the motor pulley fixed to the motor to tilt the structure to which the fixed pulley is fixed by rotation of the least one connection part when the second motor is driven,
wherein, when the motor is driven, the motor pulley tilts the fixed pulley through at least one connection part that connects the fixed pulley to the motor pulley to tilt the imaging probe and the treatment transducer together.

5. The ultrasound treatment head of claim 1, wherein the structure tilting mechanism includes:
a first gear vertically fixed to one side surface of the structure;
a motor formed to be spaced a preset interval from the third gear and configured to provide power for rotation of the entire structure; and
a second gear coupled to the motor to rotate,
wherein, when the motor is driven, the second gear directly rotates the first gear or rotates the first gear through at least one connection part that connects the first gear to the second gear to tilt the imaging probe and the treatment transducer together in the structure.

6. The ultrasound treatment head of claim 1, wherein the imaging probe rotation mechanism includes:
a fixed pulley horizontally fixed to the imaging probe;
a motor formed to be spaced a preset interval from the fixed pulley and configured to provide power for the rotation of the imaging probe alone;
a motor pulley fixed to the motor; and
a connection part configured to connect the fixed pulley fixed to the imaging probe to the motor pulley fixed to the motor to rotate the imaging probe to which the third fixed pulley is fixed by rotation of the connection part when the motor is driven,
wherein, when the motor is driven, the motor pulley rotates the fixed pulley through at least one connection part that connects the fixed pulley to the motor pulley to rotate the imaging probe alone.

7. The ultrasound treatment head of claim 1, wherein the imaging probe rotation mechanism includes:
a first gear horizontally fixed to the imaging probe;
a motor formed to be spaced a preset interval from the first gear and configured to provide power for the rotation of the entire structure; and
a second gear coupled to the motor to rotate,
wherein, when the motor is driven, the second gear directly rotates the first gear or rotates the first gear through at least one connection part that connects the first gear to the second gear to rotate the imaging probe alone.

8. The ultrasound treatment head of claim 1, further comprising:
an electronic signal generator configured to drive the treatment transducer to radiate focused ultrasound waves; and
a controller configured to drive the electronic signal generator and each of the first and second mechanisms to steer a focus of the focused ultrasound waves.

* * * * *